United States Patent [19]

Takigawa et al.

[11] Patent Number: 5,676,881
[45] Date of Patent: Oct. 14, 1997

[54] ANTIFERROELECTRIC LIQUID CRYSTAL COMPOSITION

[75] Inventors: Kenji Takigawa, Nishio; Naohisa Oyama; Hitoshi Hayashi, both of Okazaki, all of Japan

[73] Assignee: Nippon Soken Inc., Nishio, Japan

[21] Appl. No.: 591,939

[22] Filed: Jan. 23, 1996

Related U.S. Application Data

[63] Continuation of Ser. No. 418,610, Apr. 7, 1995, abandoned.

[30] Foreign Application Priority Data

Apr. 8, 1994 [JP] Japan .................................. 6-070666

[51] Int. Cl.$^6$ .............................. C09K 19/20; C07C 69/76
[52] U.S. Cl. ........................ 252/299.67; 252/299.64; 560/76; 560/83; 560/85
[58] Field of Search ..................... 252/299.64, 299.67; 560/76, 83, 85

[56] References Cited

U.S. PATENT DOCUMENTS

| | | | |
|---|---|---|---|
| 4,576,732 | 3/1986 | Isogai | 252/299.65 |
| 4,754,051 | 6/1988 | Sasaki | 252/299.01 |
| 4,921,632 | 5/1990 | Nakamura et al. | 252/299.01 |
| 4,961,874 | 10/1990 | Takeuchi | 252/299.6 |
| 5,046,823 | 9/1991 | Mori | 359/103 |
| 5,110,498 | 5/1992 | Suzuki et al. | 252/299.66 |
| 5,151,213 | 9/1992 | Reiffenrath | 252/299.6 |
| 5,171,471 | 12/1992 | Suzuki et al. | 252/299.61 |
| 5,184,847 | 2/1993 | Suzuki et al. | 252/299.65 |
| 5,204,020 | 4/1993 | Suzuki | 252/299.67 |
| 5,262,086 | 11/1993 | Suzuki et al. | 252/299.65 |
| 5,316,694 | 5/1994 | Murashiro | 252/299.61 |
| 5,330,678 | 7/1994 | Okabe et al. | 252/299.62 |
| 5,344,586 | 9/1994 | Suzuki et al. | 252/299.64 |
| 5,352,382 | 10/1994 | Johno | 252/299.65 |
| 5,356,562 | 10/1994 | Greenfield | 252/299.63 |
| 5,374,375 | 12/1994 | Yui et al. | 252/299.65 |
| 5,378,392 | 1/1995 | Murashiro | 252/299.01 |
| 5,378,396 | 1/1995 | Yui et al. | 252/299.65 |
| 5,393,460 | 2/1995 | Okabe et al. | 252/299.65 |
| 5,417,885 | 5/1995 | Suzuki | 252/299.65 |
| 5,534,190 | 7/1996 | Johno et al. | 252/299.65 |

FOREIGN PATENT DOCUMENTS

| | | |
|---|---|---|
| 330491 | 8/1989 | European Pat. Off. . |
| 339987 | 11/1989 | European Pat. Off. . |
| 0517504A1 | 12/1992 | European Pat. Off. . |
| 0525737A2 | 2/1993 | European Pat. Off. . |
| 0562627A1 | 9/1993 | European Pat. Off. . |
| 582468 A1 | 2/1994 | European Pat. Off. . |
| 0582519A1 | 2/1994 | European Pat. Off. . |
| 1-139551 | 6/1989 | Japan . |
| 1213390 | 8/1989 | Japan . |
| 1316339 | 12/1989 | Japan . |
| 1316367 | 12/1989 | Japan . |
| 2-28128 | 1/1990 | Japan . |
| 2-69440 | 3/1990 | Japan . |
| 6271852 | 9/1994 | Japan . |

OTHER PUBLICATIONS

Chandani, et al: "Tristable Switching in Surface Stabilized Ferroelectric Liquid Crystals with a Large Spontaneous Polarization", Japanese Journal of Applied Physics, vol. 27, No. 5, May 1988, pp. L729–L732.

Meyer:, "Ferroelectric Liquid Crystals; A Review", Mol.Cryst.Liq.Cryst., 1977, vol. 40, pp. 33–48.

Suzuki et al., "New Fluorine–Containing Ferroelectric Liquid Crystal Compounds Showing Tristable Switching" Liquid Crystals 6(1989) No. 2, London, GB, pp. 167–174.

Isa Nishiyama et al., "Effect of Size of the Lateral Substituent at the Chiral Centre on the Stability of Some Chiral Smectic Liquid–crystalline Phases," Journal of Materials Chemistry, vol. 3, No. 2, 1993, Cambridge, GB, pp. 149–159.

*Primary Examiner*—Shean C. Wu
*Attorney, Agent, or Firm*—Cushman, Darby & Cushman IP Group of Pillsbury Madison & Sutro LLP

[57] ABSTRACT

Antiferroelectric liquid crystals represented by the following formula (1) and (2).

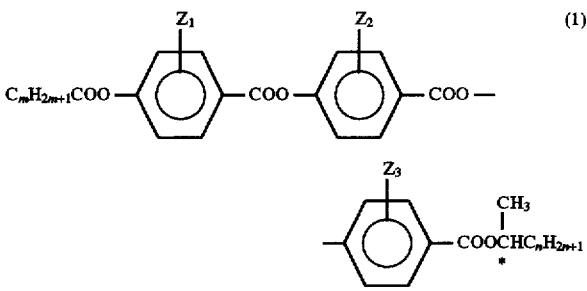

In the formula (1), each of m and n is an integer satisfying $6 \leq m \leq 14$ and $2 \leq n \leq 10$, and each of $Z_1$, $Z_2$ and $Z_3$ is independently a substituent selected from the group consisting H, F, Cl, Br, CN and $CH_3$.

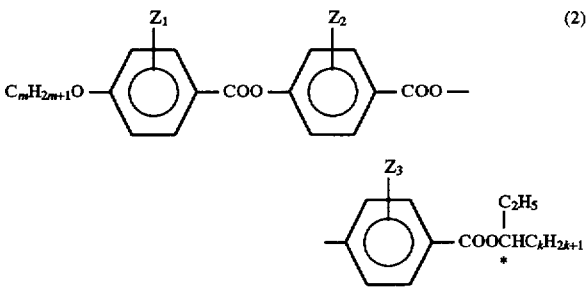

In the formula (2), each of m and n is an integer satisfying $6 \leq m \leq 14$ and $3 \leq k \leq 10$, and each of $Z_1$, $Z_2$ and $Z_3$ is independently a substituent selected from the group consisting H, F, Cl, Br, CN and $CH_3$.

6 Claims, 10 Drawing Sheets

ANTIFERROELECTRIC LIQUID CRYSTAL COMPOSITION

This is a continuation of application No. 08/418,610, filed on Apr. 7, 1995, which was abandoned upon the filing hereof.

BACKGROUND OF THE INVENTION

1. Field of the Invention

This invention relates to a novel antiferroelectric liquid crystal compound having an antiferroelectric phase (chiralsmectic $T_A^*$ phase, hereinafter abbreviated to "$SmC_A^*$ phase").

2. Description of the Related Art

Recently, liquid crystal displays have become widely used as indication elements, due to their reduced thickness, light weight, low power consumption etc. However, most of these displays use TN (Twisted Nematic) type displays comprising a nematic liquid crystal. Since the operation of TN displays is based on the anisotropy of the dielectric constant of the liquid crystal, the response speed is slow, and improvement is required.

In contrast, liquid crystal devices comprising chiralsmectic C phase (hereinafter abbreviated as "SmC* phase") liquid crystals, which are ferroelectric and were discovered by Meyer et. al., have high response speeds and memory characteristics. Thus, in order to utilize these characteristics, application of these ferroelectric liquid crystals to displays have been intensively researched. However, the good orientation and memory characteristics required for this indication method are difficult to realize in practice. Many problems remain to be solved, such as sensitivity to external shocks etc.

On the other hand, recently, an antiferroelectric phase (hereinafter abbreviated as "$SmC_A^*$ phase") has been discovered by Chandani et. al. which shows three stable states on the lower temperature side of said SmC* phase. This antiferroelectric liquid crystal shows a thermodynamically stable phase wherein dipoles are arranged in antiparallel in every adjacent layer, and exhibits an electric field-induced phase transition between the antiferroelectric phase and the ferroelectric phase which is characterized by a clear threshold and double hysteresis in response to applied voltage. Investigations on indication methods utilizing this switching behavior have already begun.

SUMMARY OF THE INVENTION

Figure 1:
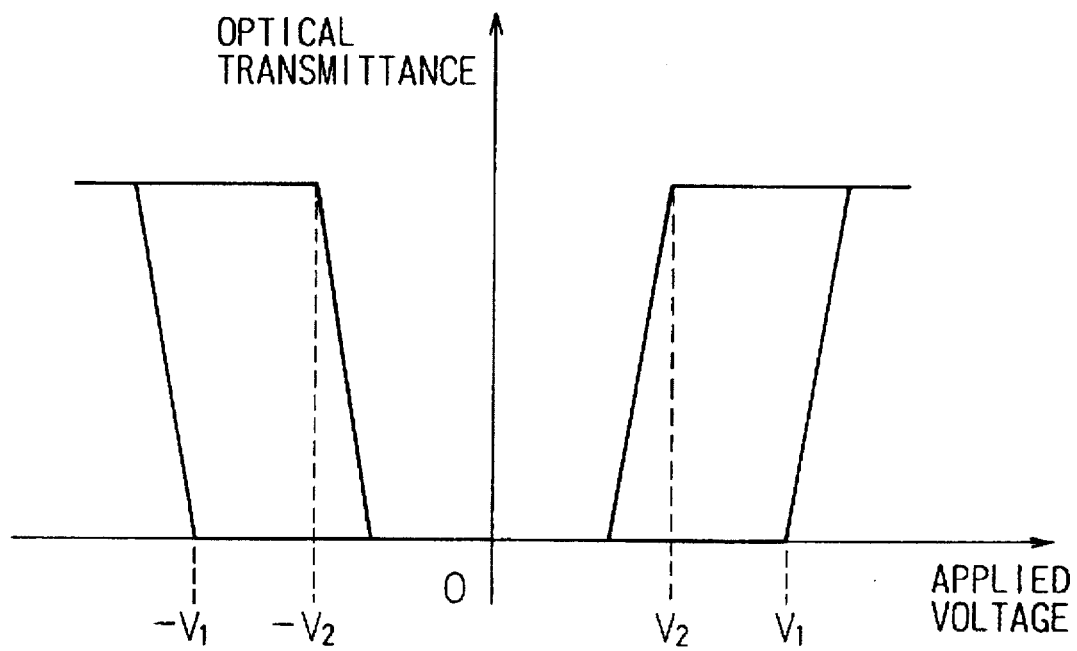
FIG. 1 is a schematic diagram indicating an optical response of an antiferroelectric liquid crystal to an applied voltage.
Figure 2:
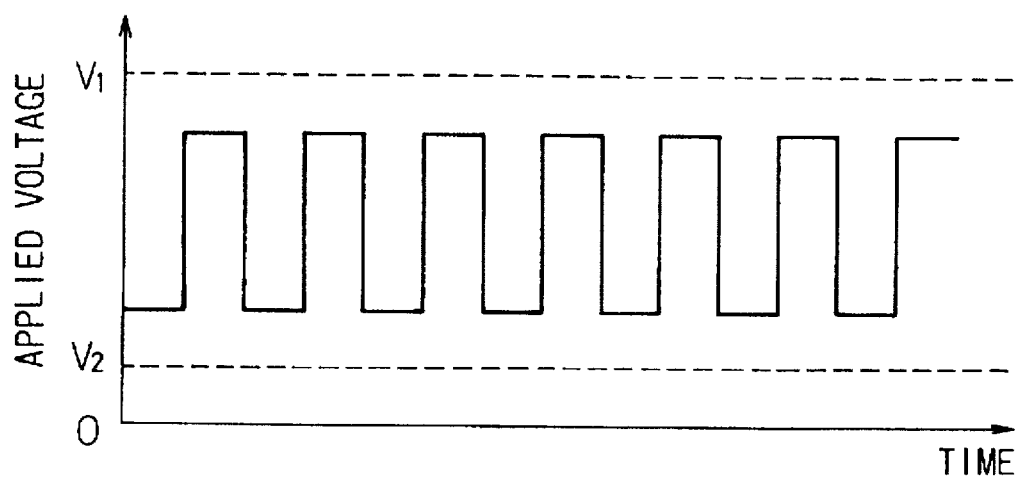
FIG. 2 is a diagram indicating a rectangular wave between each threshold voltage ($V_1$ and $V_2$) at voltage increasing time and voltage decreasing time for holding brightness and darkness indicating states of a liquid crystal.

The antiferroelectric liquid crystal indicates the double hysteresis characteristics of its optical response to the applied voltage as shown in FIG. 1. In order to realize a response of darkness to brightness, a voltage larger than $V_1$ is applied and in order realize a response of brightness to darkness, a voltage smaller than $V_2$ is applied. In order to maintain a bright or dark state, an alternative rectangular wave is continuously applied. In this time, if the width $V_1-V_2$ is narrow, during the brightness indication holding or darkness holding period a change to the other state sometimes occurs. Therefore, an antiferroelectric liquid crystal having double hysteresis characteristics with a large $V_1-V_2$ width, i.e. an excellent indication characteristic, is required. However, at present, there are few antiferroelectric liquid crystals, particularly, there are few antiferroelectric liquid crystals having excellent indication characteristics. An object of this invention is to provide novel antiferroelectric liquid crystals having excellent indication characteristics.

This invention relates to novel antiferroelectric liquid crystals represented by the following formula (1) and (2).

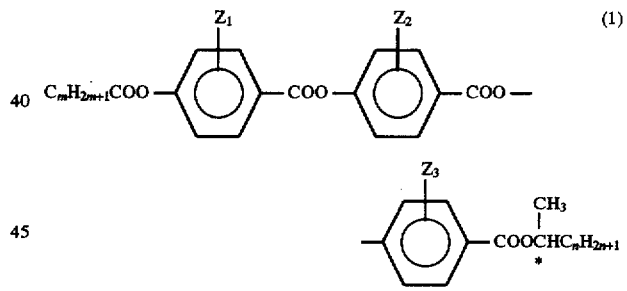

In the formula (1), each of m and n is an integer satisfying $6 \leq m \leq 14$ and $2 \leq n \leq 10$, and each of $Z_1$, $Z_2$ and $Z_3$ is independently a substituent selected from the group consisting of H, F, Cl Br, CN and $CH_3$.

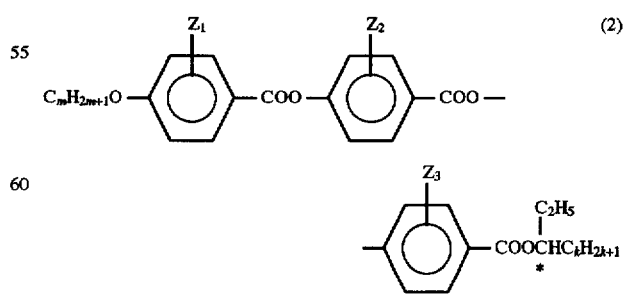

In the formula (2), each of m and n is an integer satisfying $6 \leq m \leq 14$ and $3 \leq k \leq 10$, and each of $Z_1$, $Z_2$ and $Z_3$ is independently a substituent selected from the group consisting of H, F, Cl, Br, CN and $CH_3$.

DETAILED EXPLANATION OF THE INVENTION

The liquid crystal represented by formula (1) is preferably a compound wherein each of $Z_1$, $Z_2$ and $Z_3$ is independently H or F. More preferably it is represented by the following formula (3), wherein $Z_3$ is H or F:

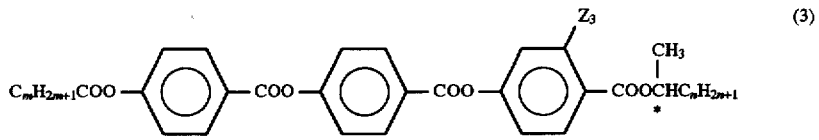

(3)

The liquid crystal represented by formula (2) is preferably a compound wherein each of $Z_1$, $Z_2$ and $Z_3$ is independently H or F. More preferably it is represented by the following formula (4):

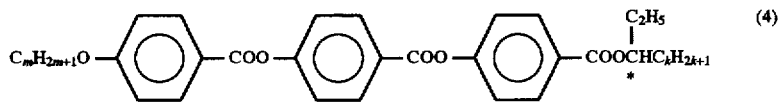

(4)

A method of synthesizing the compounds of this invention will be now shown as follows.

(1) An aliphatic acid chloride and p-hydroxybenzoic acid or a derivative thereof are reacted in the presence of triethyl amine to obtain 4-alkylcarbonyloxy benzoic acid or a derivative thereof. Then it is changed to 4-alkylcarbonyloxy benzoic acid chloride or a derivative thereof by thionyl chloride. The resulting acid chloride is reacted with p-hydroxybenzoic acid or a derivative thereof in the presence of triethyl amine to give 4-(4-alkylcarbonyloxy phenyl carbonyloxy) benzoic acid or a derivative thereof. Then the resulting acid is changed by using thionyl chloride to 4-(4-alkylcarbonyloxy phenyl carbonyloxy) benzoic acid chloride or a derivative thereof.

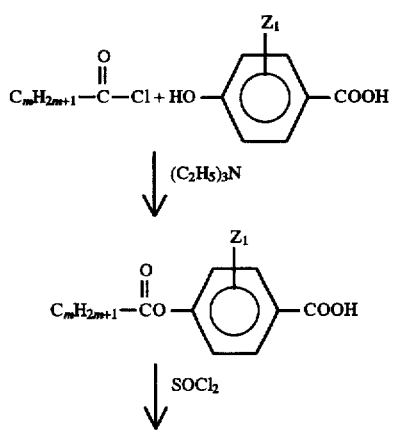

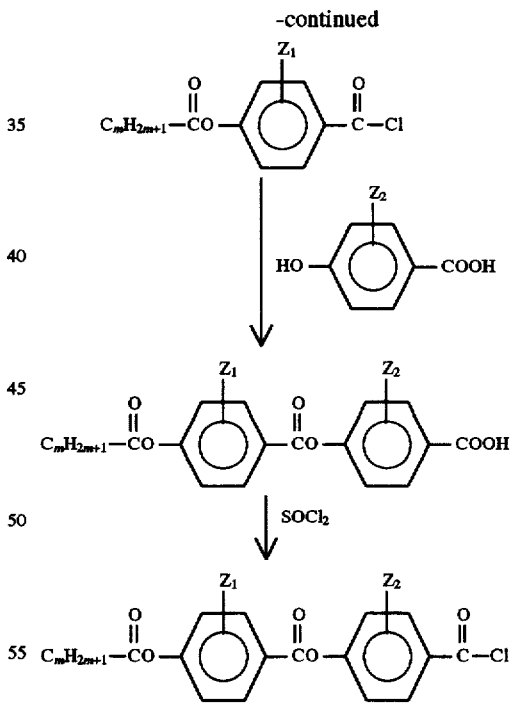

(2) 4-benziloxy benzoic acid chloride or a derivative thereof and optically active 2-alkanol is reacted in the presence of triethyl amine to obtain 1-methyl-1-alkyl-4-benziloxy benzoate or a derivative thereof. The resulting compound is subjected to hydrogenolysis to give 1-methyl-1-alkyl-4-hydloxybenzoate or a derivative thereof.

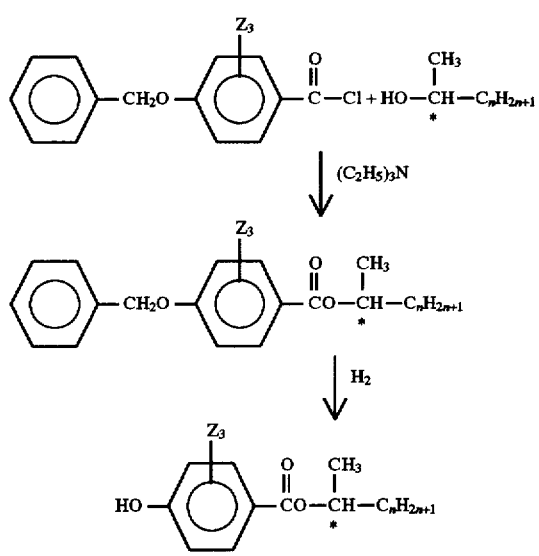

chloride is reacted with p-hydroxy benzoic acid or a derivative thereof in the presence of triethylamine to obtain 4-(4-alkyloxy phenyl carbonyloxy) benzoic acid or a derivative thereof. The thus obtained compound is reacted with thionyl chloride to provide 4-(4-alkyloxy phenyl carbonyloxy) benzoic acid chloride or a derivative thereof.

(5) The acid chloride obtained in (4) and 1-methyl-1-alkyl-4-hydroxy benzoate or a derivative thereof obtained in (2) are reacted to obtain 4-(1-methyl-1-alkyloxy carbonyl) phenyl-4-(4-alkyloxy phenyl carbonyloxy) benzoate or a derivative thereof.

(3) A chloride obtained in (1) and phenol obtained in (2) are reacted in the presence of triethylamine to obtain 4-(1-methyl-1-alkyloxycarbonyl) phenyl-4-(4-alkylcarbonyloxy phenyl carbonyloxy) benzoate or a derivative thereof.

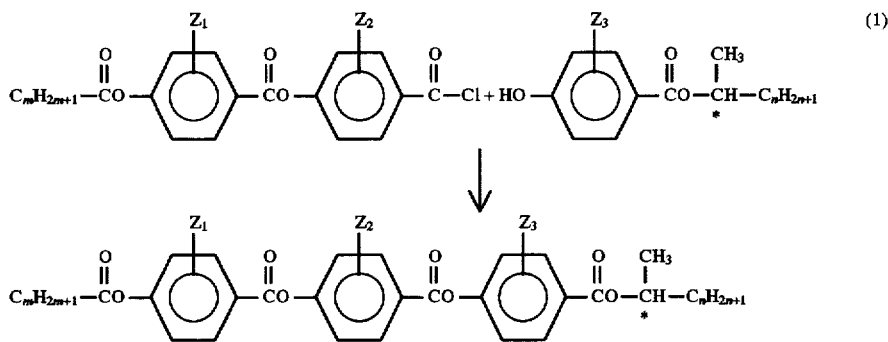

(1)

(4) p-alkyloxy benzoic acid or a derivative thereof and thionyl chloride are reacted to provide p-alkyloxy benzoic acid chloride or a derivative thereof. The thus obtained acid

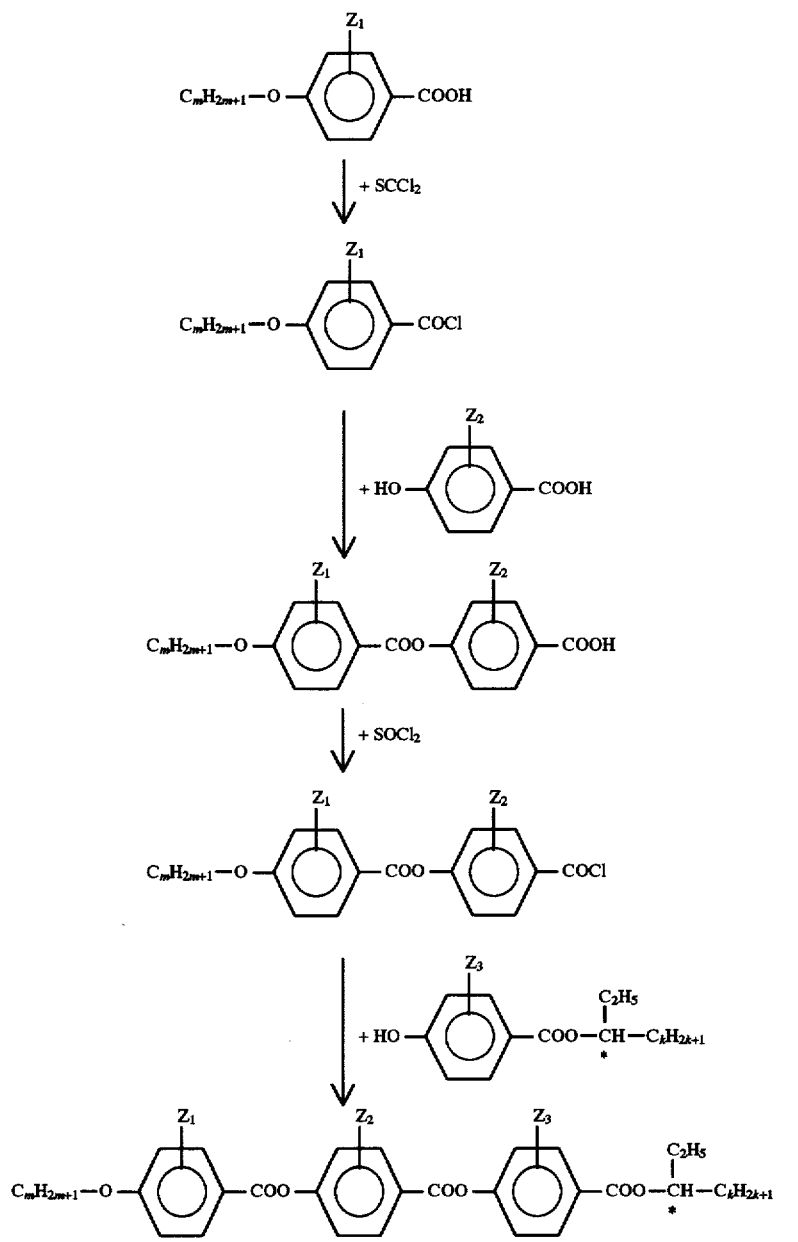

This invention provides novel antiferroelectric liquid crystals having an excellent indicating characteristics. Further, the novel antiferroelectric liquid crystal compounds provided by this invention can be utilized for making an indicating element using a switching behavior peculiar to the antiferroelectric phase of the liquid crystal compounds.

Hereinafter this invention will be illustrated by examples, to which it is in no way limited.

EXAMPLE 1

3-fluoro-4-(1-methylheptyloxy carbonyl) phenyl-4-(4-nonanoiloxy phenyl carbonyloxy) benzoate (1) Synthesis of 2-fluoro-4-benziloxy benzoic acid-1-methylheptyl ester:

(2)

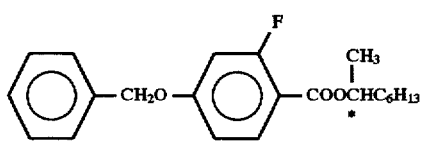

2.7 g of 2-fluoro-4-benziloxy benzoic acid chloride was dissolved in 30 ml of dichloromethane, to which was dropwise added under cooling by ice a solution provided by dissolving 1.3 g of optically active 2-octanol, 0.3 g of dimethylaminopyridine and 1.5 g of triethylamine in 50 ml of dichloromethane. The thus obtained reaction mixture was restored to room temperature and reacted overnight. The resulting mixture was put into ice water and extracted by dichloromethane. The thus obtained dichloromethane phase was washed successively by dilute aqueous hydrochloric acid, water, aqueous 1N sodium carbonate and water, and was dried with magnesium sulfate anhydride. Thereafter the solvent was distilled off to leave a coarse product. The coarse product was treated by toluene-silica gel chromatography and recrystallized in ethanol to give 2.0 g of a target compound.

(2) Synthesis of 2-fluoro-4-hydroxy benzoic acid-1-methylheptyl ester:

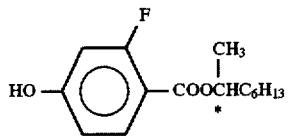

The compound obtained in (1) was dissolved in 100 ml of methanol, to which 0.25 g of 10% Pd carrying carbon was added; thereafter it was subjected to hydrogenolysis under hydrogen atmosphere, to provide 1.3 g of target compound.

(3) Synthesis of 4-nonanoiloxy benzoic acid:

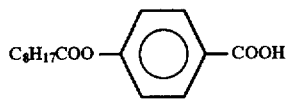

3 g of p-hydroxy benzoic acid and 2.4 g of triethyl amine were dissolved in 30 ml of dichloromethane, to which 4.0 g of nonanoil chloride and 0.2 g of dimethylamino pyridine was added, and stirred for 20 hours at room temperature. To this mixture a dilute hydrochloric acid was added. Thereafter, the organic layer was separated from the resulting mixture with a separatory funnel. The organic solvent was distilled off, and the residue was washed with n-hexane and dried to give 4 g of a target compound.

(4) Synthesis of 4-nonanoiloxy benzoic acid chloride:

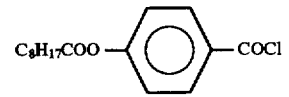

4.0 g of the compound synthesized in (3) was put into 10 g of thionyl chloride and further an extremely small amount of N,N-dimethylformamide was added thereto, and the resulting mixture was subjected to reflux for 4 hours. An excess of thionyl chloride was distilled off to give 3.8 g of an objective compound.

(5) Synthesis of 4-carboxyphenyl-4-nonanoiloxy benzoate:

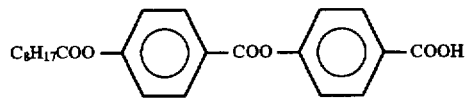

1.5 g of p-hydroxy benzoic acid and 1.1 g of triethyl amine were dissolved in 30 ml of dichloromethane. To this solution, 3 g of the compound synthesized in (4) and 0.3 g of dimethyl aminopyridine were added, and the resulting mixture was stirred for 20 hours at room temperature. To the resulting mixture dilute hydrochloric acid was added. Thereafter, the organic layer was separated from the resulting mixture with a separatory funnel. From the separated organic layer the solvent was distilled off, and the residue was washed with n-hexane and dried to give 2 g of a target compound.

(6) Synthesis of 4-(4-n-nonanoiloxy phenyl carbonyloxy) phenyl carbonyl chloride:

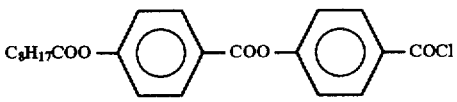

2 g of the compound synthesized in (5) was added to 10 g of thionyl chloride and further an extremely small amount of N,N-dimethylformamide was added thereto, and the mixture was subjected to reflux for 4 hours. An excess of thionyl chloride was distilled off to provide 1.8 g of a target compound.

(7) Synthesis of 3-fluoro-4-(1-methylheptyloxy carbonyl) phenyl-4-(4-nonanoiloxy phenyl carbonyloxy) benzoate:

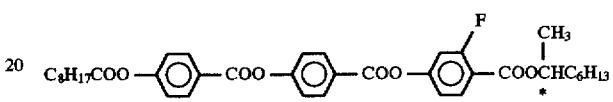

0.5 g of 2-fluoro-4-hydroxy benzoic acid-1-methylheptyl ester synthesized in (2) and 0.16 g of triethylamine were dissolved into 30 ml of dichloromethane. To the resulting solution, a solution of 0.7 g of 4-(4-n-nonanoiloxy phenyl carbonyloxy) phenyl carbonyl chloride synthesized in (6) in 30 ml of dichloromethane was added dropwise. To the resulting solution 0.05 g of dimethylaminopyridine was added and stirred overnight at room temperature. The resulting reaction mixture was added to water and the resulting solution was adjusted to neutral pH, thereafter the dichloromethane layer was separated. The separated layer was dried by magnesium sulfate anhydride, followed by distilling off the dichloromethane. The residue was refined with silica gel column chromatography to give 0.1 g of an objective compound.

Figure 3:
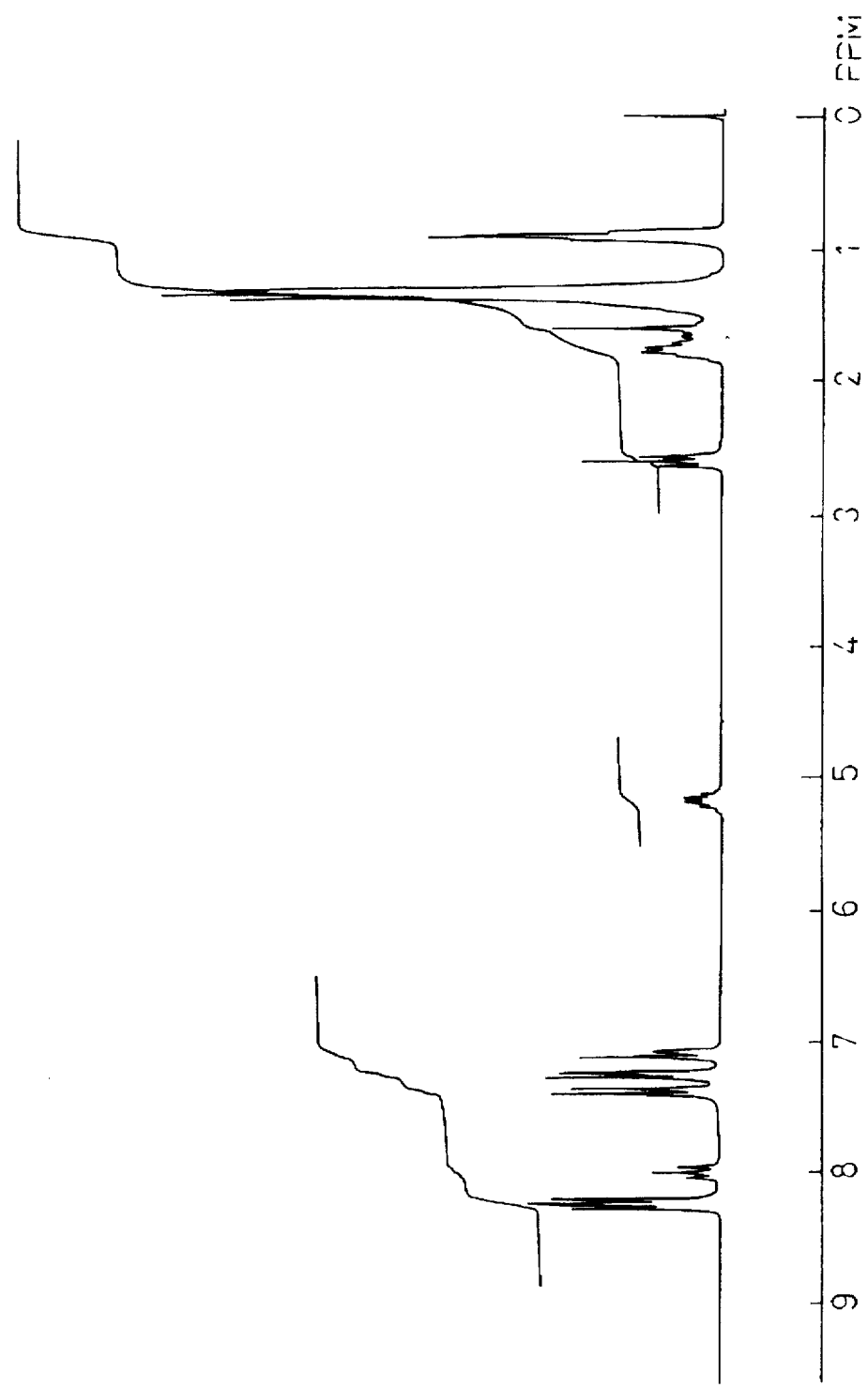
FIG. 3 is an NMR spectrum of the compound obtained in Example 1.

The NMR spectrum of the compound obtained in (7) is shown in FIG. 3. From the spectrum, the obtained compound was identified as the target compound.

ITO electrode substrates were spin coated with polyimide film and subjected to rubbing treatment, thereafter, two of the resulting substrates were arranged to face each other so that the rubbing directions were parallel, to form a liquid crystal cell having a cell thickness of 2.0 μm. The liquid crystal obtained in Example 1 was filled into the liquid crystal cell in its isotropic phase to make a liquid crystal thin film cell. The thus made liquid crystal cell was placed in a polarization microscope having a hot stage, wherein two polarizing plates were crossed and wherein a dark field is formed in the state of an applied voltage of 0V. In this condition, the increasing and decreasing temperature speed was set at 2° C./min. and the phase transition temperatures of the liquid crystal in the temperature increasing process and temperature decreasing process were determined. The phase series obtained by the observation of this polarization microscope having a hot stage is as follows.

$$C_{ry} \frac{74.1}{50.0} S_{CA} * \frac{112.0}{110.0} S_A \frac{142.5}{137.6} I_{so}$$

(Upper numeral, temperature increase; lower numeral, temperature decrease)

From this phase series, it is apparent that the compound is an antiferroelectric liquid crystal.

EXAMPLE 2

4-(1-ethylheptyloxycarbonyl) phenyl-4-(4-octyloxy phenyl carbonyloxy) benzoate (1) Synthesis of 1-heptyl-4-hydroxy benzoate:

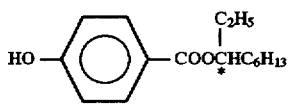

The same reactions (1) and (2) of Example 1 were carried out except that in place of optically active 2-fluoro-4-benziloxy benzoic acid chloride and 2-octanol, 4-benziloxy benzoic acid chloride and optically active 3-nonanol were used, respectively, to provide 1.2 g of a target compound.

(2) Synthesis of p-octyloxy benzoic acid chloride:

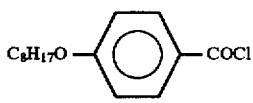

5.0 g of p-octyloxy benzoic acid was added to 10 g of thionyl chloride and an extremely small amount of N,N-dimethyl formamide was added thereto, and the resulting mixture was refluxed for 4 hours. An excess of thionyl chloride was distilled off to give 5.1 g of a target compound.

(3) Synthesis of 4-(4-octyloxy phenyl carbonyloxy) benzoic acid:

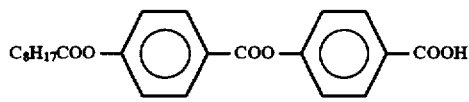

2.4 g of p-hydroxy benzoic acid and 1.9 g of triethylamine were dissolved into 30 ml of dichloromethane. To this solution 5.1 g of the acid chloride synthesized in (2) and 0.6 g of dimethylamino pyridine were added and the mixture was stirred for 20 hours. To this reaction mixture dilute hydrochloric acid was added and from the resulting mixture the organic layer was separated with a separatory funnel. The solvent was distilled off the organic layer. The residue was washed with n-hexane and dried to give 5 g of a target compound.

(4) Synthesis of 4-(4-octyloxyphenyl carbonyloxy) benzoic acid chloride:

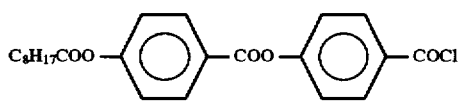

5.0 g of the compound synthesized in the above (3) was added to 10 g of thionyl chloride and an extremely small amount of N,N-dimethyl formamide was added thereto, and the resulting mixture was refluxed for 4 hours. An excess of thionyl chloride was distilled off to give 5.1 g of a target compound.

(5) Synthesis of 4-(ethylheptyloxy carbonyl) phenyl-4-(4-nonanoiloxy phenyl carbonyloxy) benzoate:

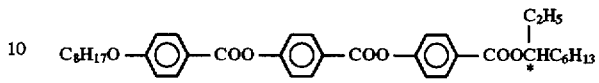

0.5 g of 1-ethylheptyl-4-hydroxy benzoate synthesized in (2) and 0.19 g of triethylamine were dissolved into 30 ml of dichloromethane. To this solution, a solution of 0.7 g of 4-(4-n-octyloxy phenyl carbonyloxy) benzoic acid chloride synthesized in (4) in 30 ml of dichloromethane was added dropwise. To the resulting solution 0.06 g of dimethylaminopyridine was added and stirred overnight at room temperature. The resulting reaction mixture was put into water and the resulting solution was adjusted to neutral pH, thereafter the dichloromethane layer was separated. The separated layer was dried with magnesium sulfate anhydride, followed by distilling off of the dichloromethane. The residue was refined with a silica gel column chromatograph to give 0.1 g of a target compound.

Figure 4:
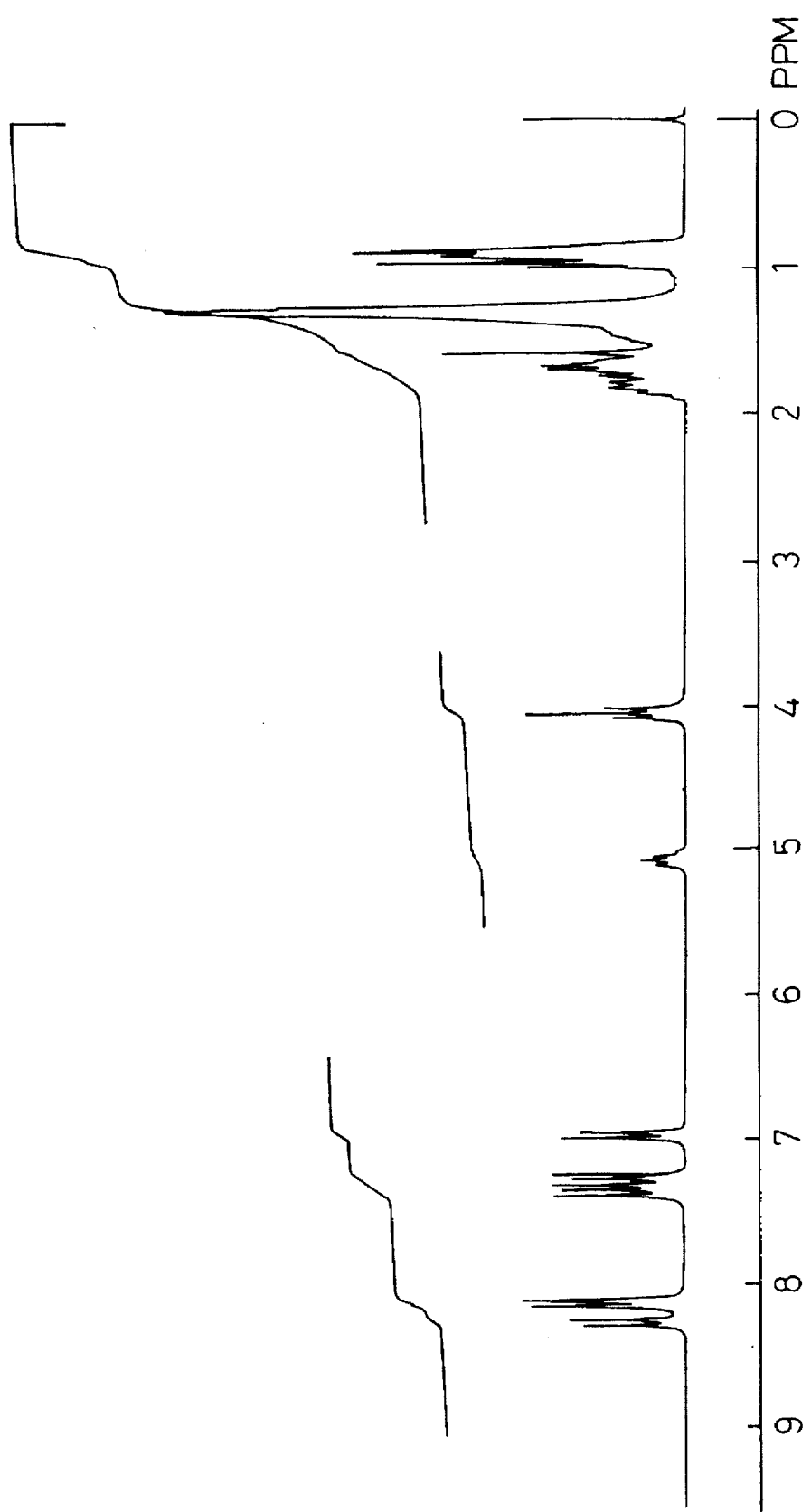
FIG. 4 is an NMR spectrum of the compound obtained in Example 2.

The NMR spectrum of the compound obtained in (5) is shown in FIG. 4. From the spectrum, the obtained compound was identified as the objective compound.

The obtained compound was observed with a polarization microscope having a hot stage in the same way as in Example 1. The obtained phase series are as follows.

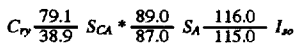

(Upper numeral, temperature increase; lower numeral, temperature decrease)

From this phase series, it is apparent that the compound is an antiferroelectric liquid crystal.

EXAMPLE 3

3-fluoro-4-( 1-methylbutyloxy carbonyl ) phenyl-4-( 4-undecanoiloxy phenyl carbonyloxy) benzoate

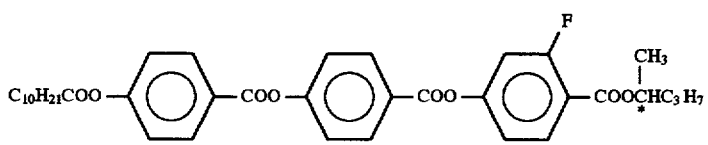

The same reaction as in Example 1 was carried out, except that optically active 2-pentanol was used in place of the optically active 2-octanol used in (1) of Example 1, and undecanoil chloride was used in place of nonanoil chloride used in (3) of Example 1, to give 0.1 g of a target compound.

Figure 5:
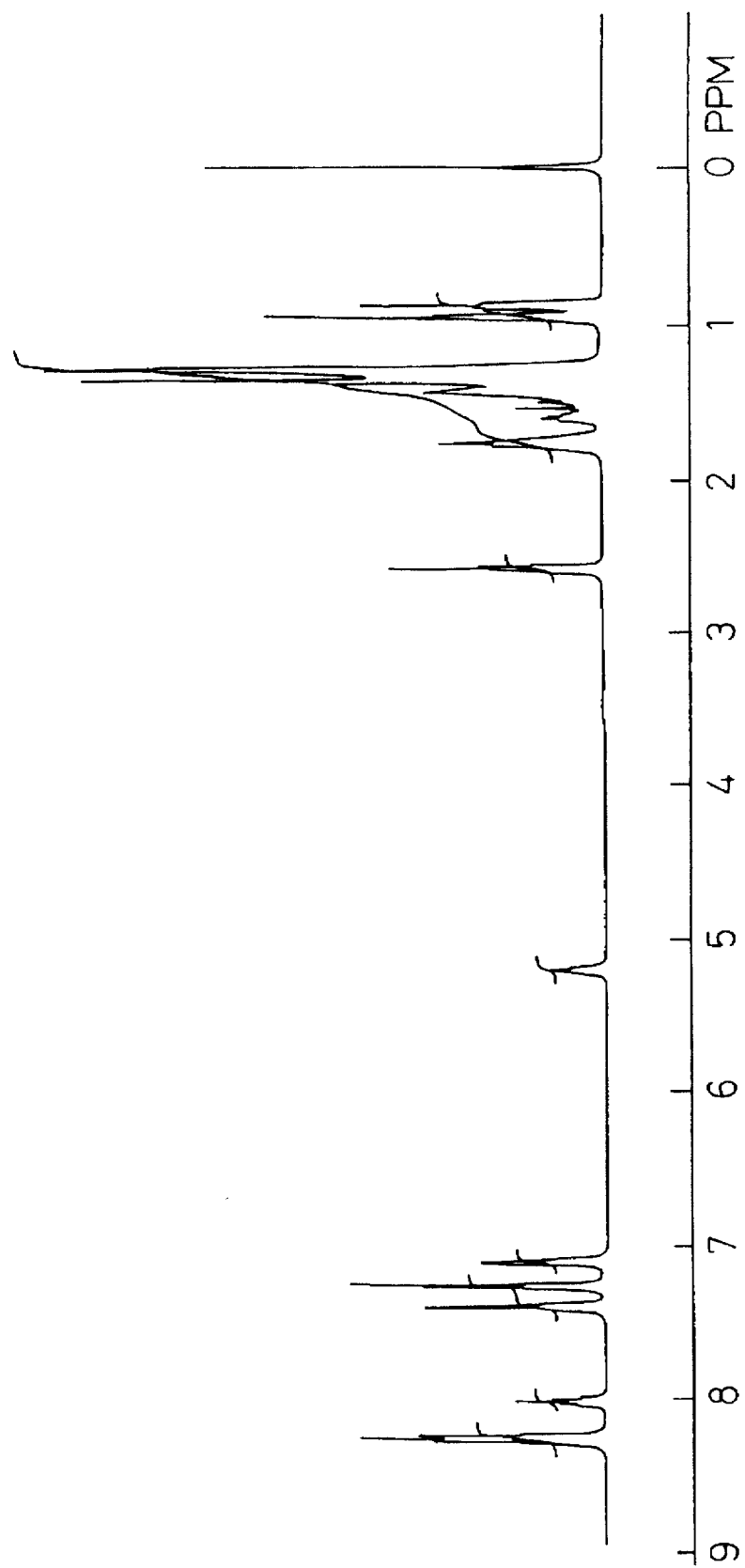
FIG. 5 is an NMR spectrum of the compound obtained in Example 3.

The NMR spectrum of the compound thus obtained is shown in FIG. 5. From the spectrum, the obtained compound was identified as the objective compound.

The obtained compound was observed with a polarization microscope having a hot stage in the same way as in Example 1. The obtained phase series are as follows.

$$C_ry \frac{72.7}{47.2} S_{CA} * \frac{123.7}{121.7} S_X \frac{125.5}{123.5} S_A \frac{153.4}{153.7} I_{so}$$

(Upper numeral, temperature increase; lower numeral, temperature decrease)

From this phase series, it is apparent that the compound is an antiferroelectric liquid crystal.

EXAMPLE 4

4-(methylheptyloxy carbonyl) phenyl-4-(4-decanoiloxy phenyl carbonyloxy) benzoate

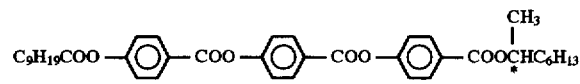

The same reaction as in Example 1 was carried out, except that 4-benziloxy benzoil chloride was used in place of 2-fluoro-4-benziloxy benzoil chloride used in (1) of Example 1, and decanoil chloride was used in place of nonanoil chloride used in (3) of Example 1, to give 0.09 g of a target compound.

Figure 6:
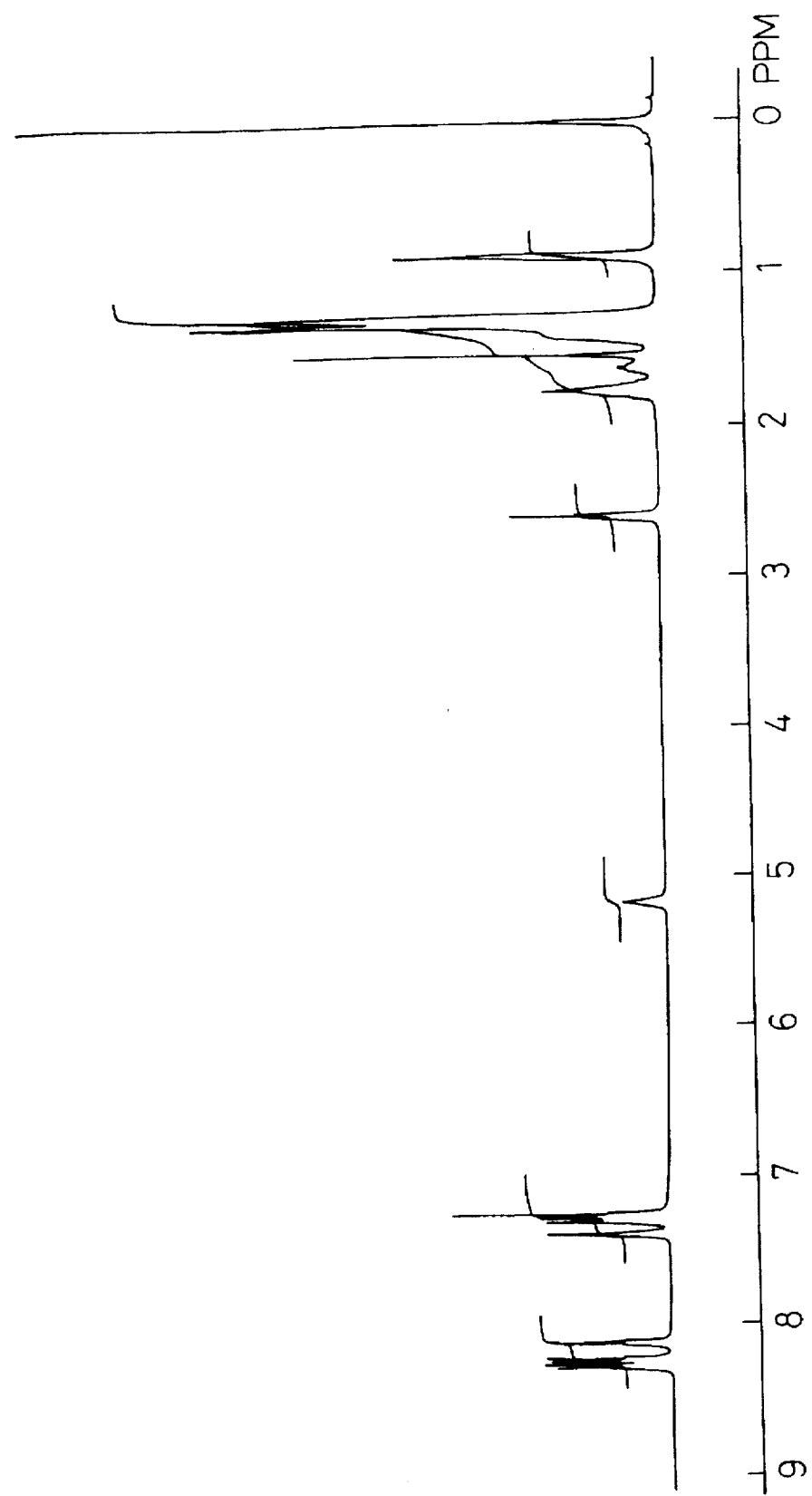
FIG. 6 is an NMR spectrum of the compound obtained in Example 4.
Figure 7:
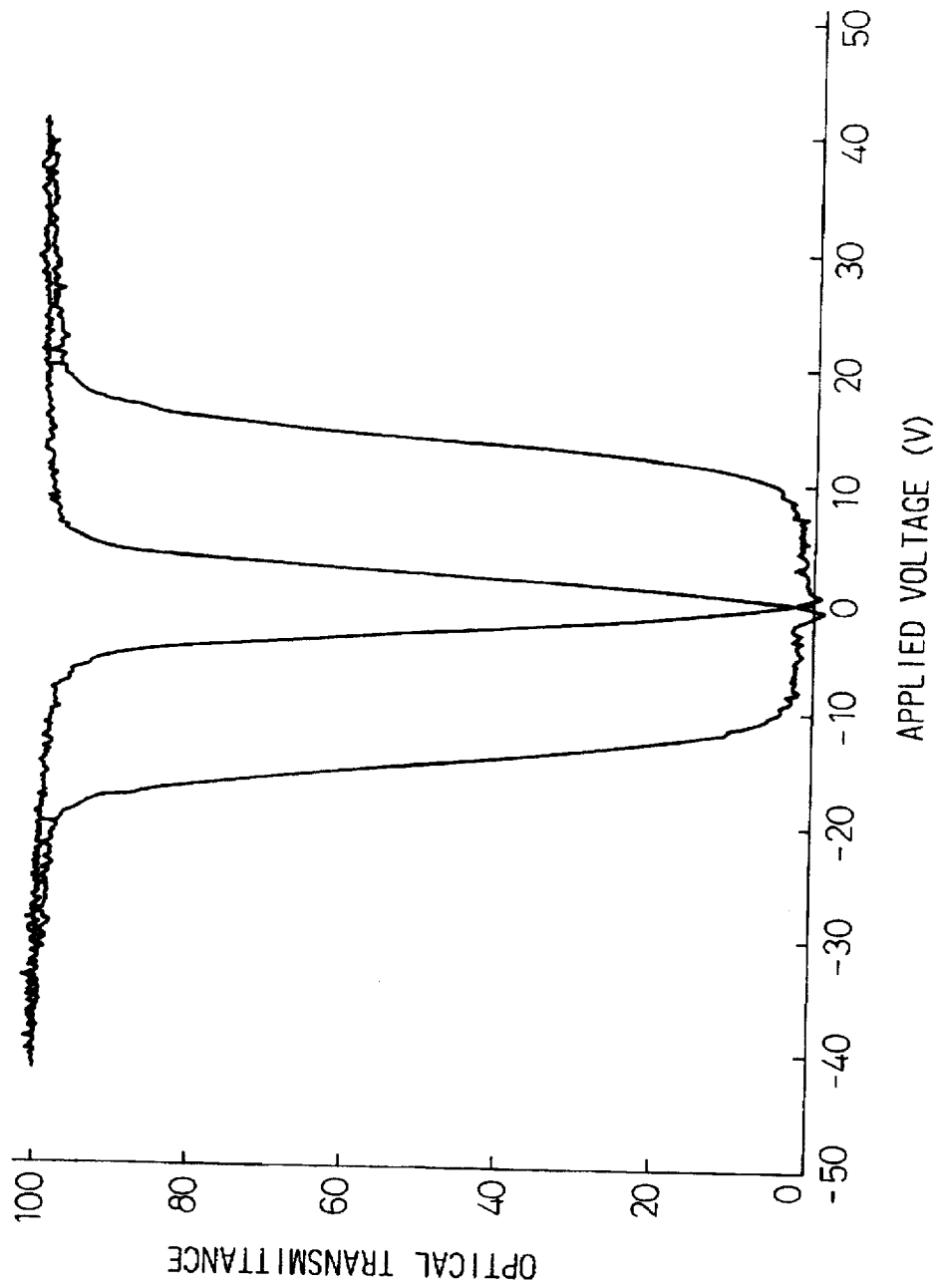
FIG. 7 is a diagram indicating double hysteresis characteristics between applied voltage and optical transmittance of a conventional liquid crystal.
Figure 8:
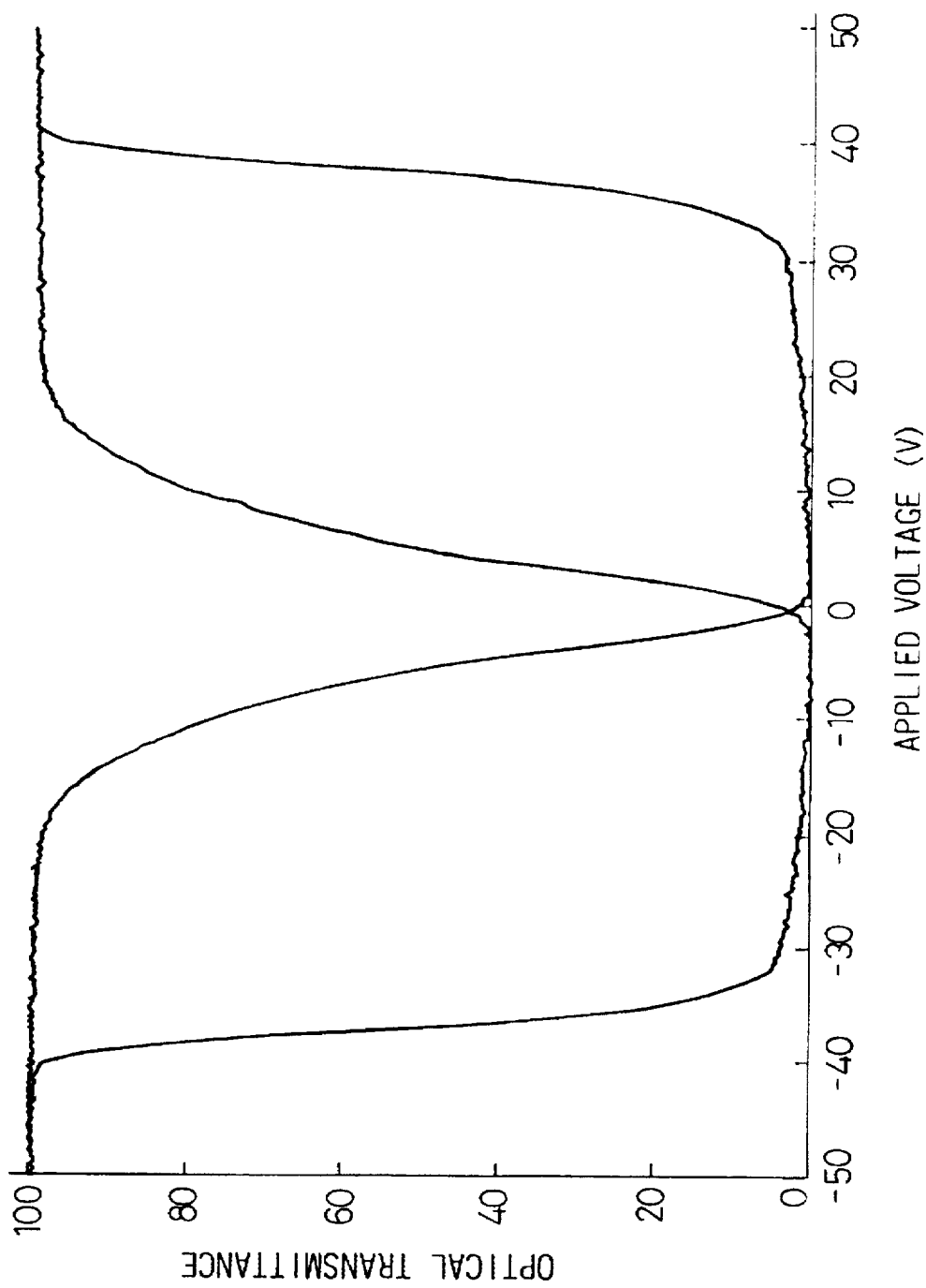
FIG. 8 is a diagram indicating double hysteresis characteristics between applied voltage and optical transmittance of the liquid crystal of Example 1.
Figure 9:
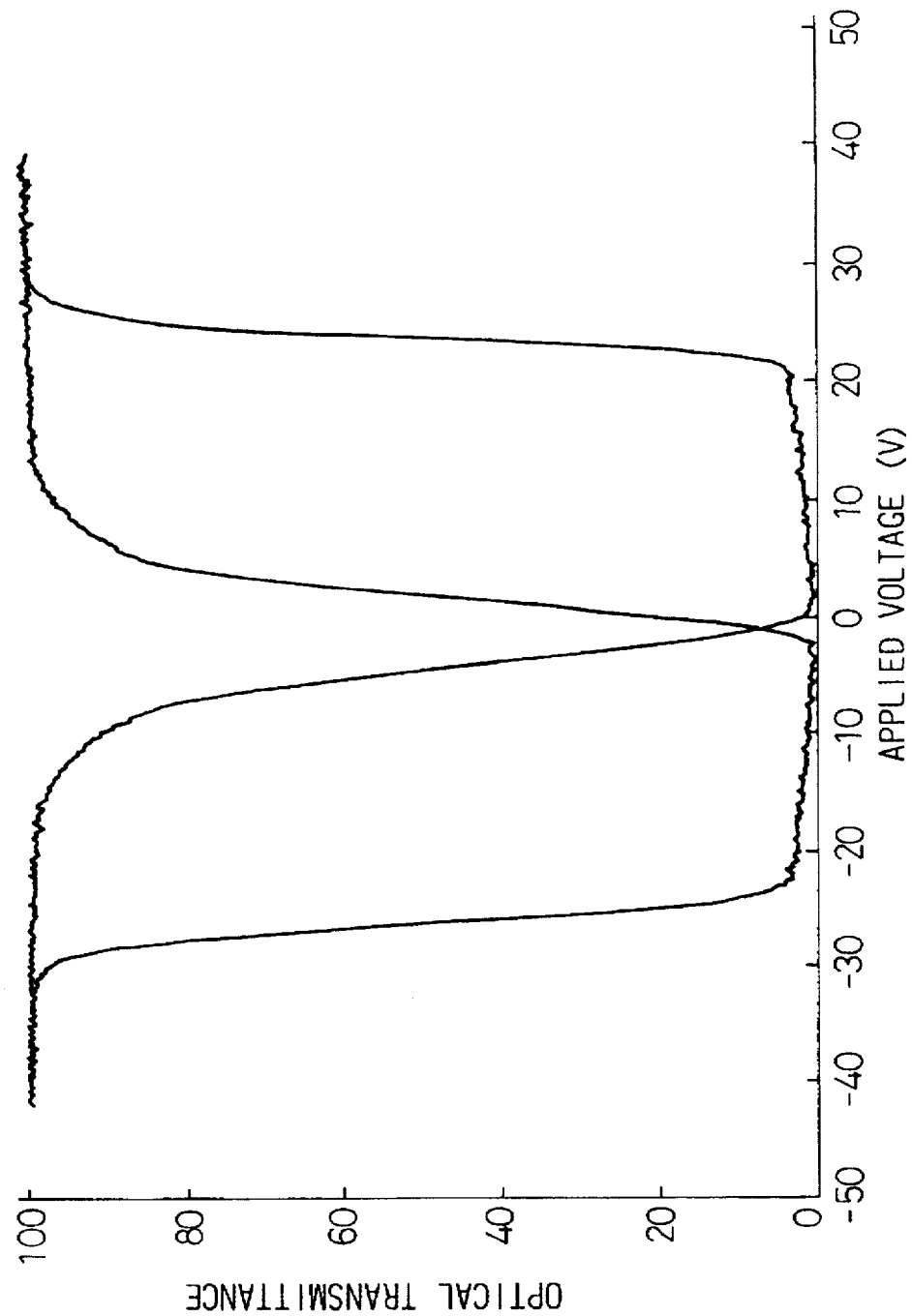
FIG. 9 is a diagram indicating double hysteresis characteristics between applied voltage and optical transmittance of the liquid crystal of Example 2.
Figure 10:
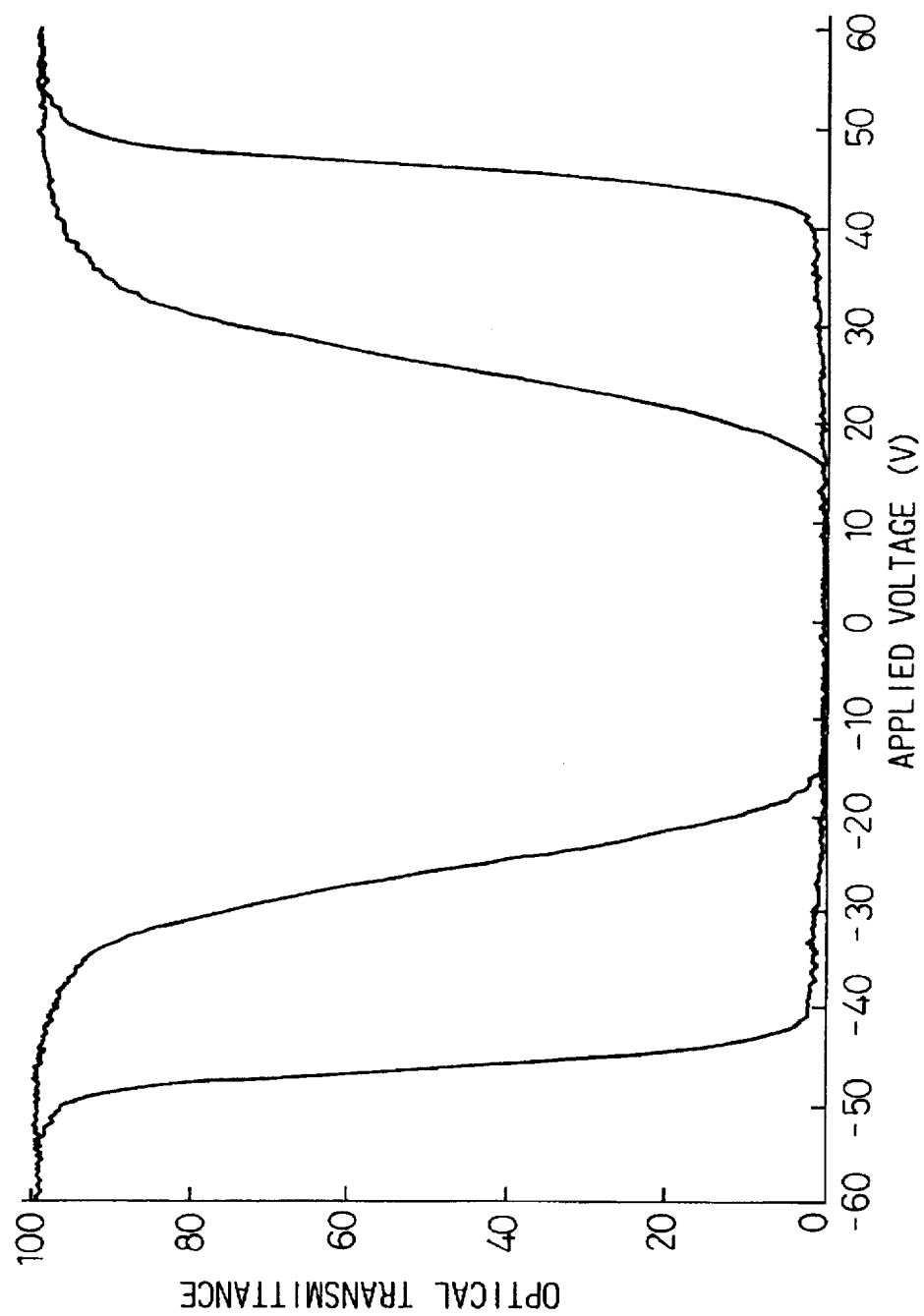
FIG. 10 is a diagram indicating a double hysteresis characteristics between applied voltage and optical transmittance of the liquid crystal of Example 3.
Figure 11:
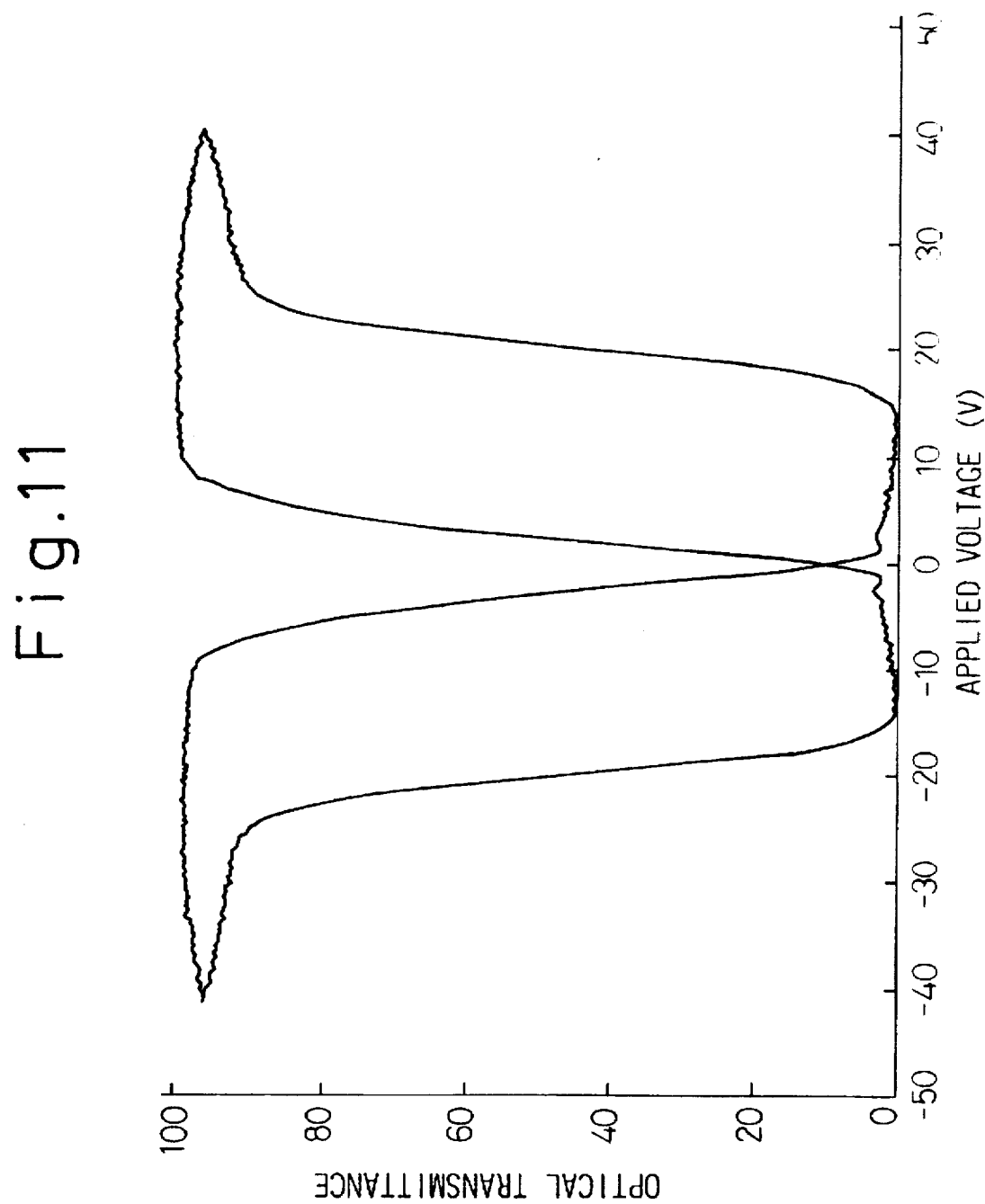
FIG. 11 is a diagram indicating double hysteresis characteristics between applied voltage and optical transmittance of the liquid crystal of Example 4.

The NMR spectrum of the compound thus obtained is shown in FIG. 6. From the spectrum, the obtained compound was identified as the target compound.

The obtained compound was observed with a polarization microscope having a hot stage in the same way as in Example 1. The obtained phase series are as follows.

$$C_ry \frac{82.9}{65.1} S_{CA} * \frac{99.5}{96.3} S_A \frac{141.0}{141.0} I_{so}$$

(Upper numeral, temperature increase; lower numeral, temperature decrease)

From this phase series, it is apparent that the compound is an antiferroelectric liquid crystal.

EXAMPLE 5

Prior Example 4-(methylheptyloxy carbonyl) phenyl-4-(4-octyloxy phenyl carbonyloxy) benzoate

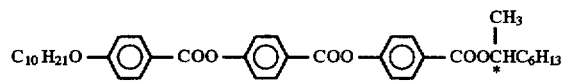

The obtained compound was observed with a polarization microscope having a hot stage in the same way as in Example 1. The obtained phase series are as follows.

$$C_ry \frac{101.0}{96.0} S_{CA} * \frac{117.2}{114.4} S_A \frac{136.9}{135.5} I_{so}$$

(Upper numeral, temperature increase; lower numeral, temperature decrease)

From this phase series, it is apparent that the compound is an antiferroelectric liquid crystal.

For the liquid crystals of Examples 1 to 5, the liquid crystal cells used for determination of phase series were placed in a polarization microscope having a hot stage, wherein two polarizing plates were crossed and wherein a dark field is formed in the state of an applied voltage of 0V. To the liquid crystal cells, chopping waves of ±40V, 1 Hz were applied and optical transmittances were determined. The obtained hysteresis measurements between applied voltage and optical transmittance are shown in FIGS. 7 to 11. Further, thresholds of voltage increasing time and voltage decreasing time, and the temperature at the time of determining the thresholds are shown in Table 1.

TABLE 1

|  | $V_1$ | $V_2$ | $V_1$-$V_2$ | T-$T_{SCA}$ (°C.) |
|---|---|---|---|---|
| Example 5 | 8 | 6 | 2 | −40 |
| Example 1 | 31 | 18 | 13 | −30 |
| Example 2 | 21 | 11 | 10 | −40 |
| Example 3 | 42 | 34 | 8 | −15 |
| Example 4 | 15 | 8 | 7 | −30 |

Unit: V,
T-$T_{SCA}$: (hysteresis temperature) − ($S_{CA}$* phase upper limit temperature From this Table, it is apparent that Examples 1 to 4 have larger $V_1$–$V_2$ in comparison to the prior example (Example 5), and have excellent indication characteristics.

We claim:

1. An antiferroelectric liquid crystal represented by the following formula (1):

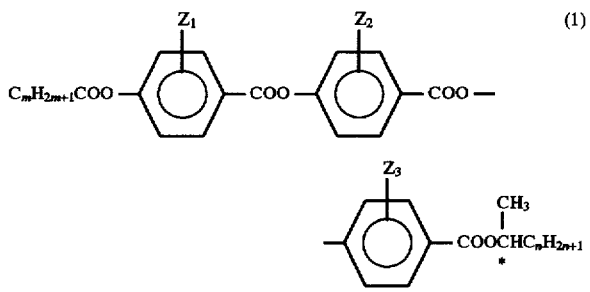

In the formula (1), each of m and n is an integer satisfying 6≦m≦14 and 2≦n≦10, and each of $Z_1$, $Z_2$ and $Z_3$ is independently a substituent selected from the group consisting H, F, Cl, Br, CN and $CH_3$.

2. The antiferroelectric liquid crystal according to claim 1, wherein each of $Z_1$, $Z_2$ and $Z_3$ is independently H or F.

3. The antiferroelectric liquid crystal according to claim 2, wherein the liquid crystal is represented by the following formula (3), wherein $Z_3$ is H or F:

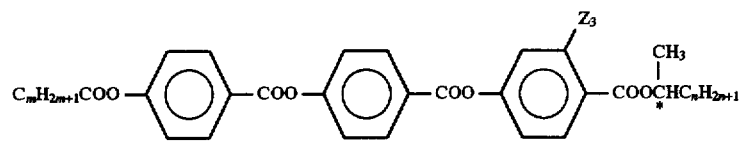
(3)

4. An antiferroelectric liquid crystal represented by the following formula (2):

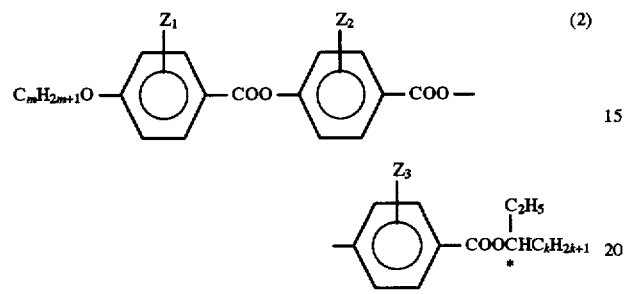
(2)

In the formula (2), each of m and n is an integer satisfying $6 \leq m \leq 14$ and $3 \leq k \leq 10$, and each of $Z_1$, $Z_2$ and $Z_3$ is independently a substituent selected from the group consisting H, F, Cl, Br, CN and $CH_3$.

5. The antiferroelectric liquid crystal according to claim 4, wherein each of $Z_1$, $Z_2$ and $Z_3$ is independently H or F.

6. The antiferroelectric liquid crystal according to claim 5, wherein the liquid crystal is represented by the following formula (4):

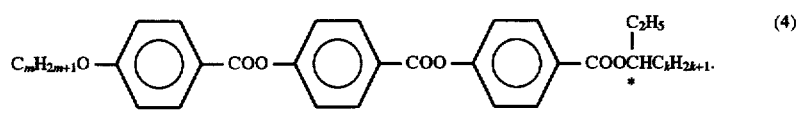
(4)

\* \* \* \* \*